(12) United States Patent
Kaltschmidt et al.

(10) Patent No.: US 7,493,155 B2
(45) Date of Patent: Feb. 17, 2009

(54) NON-INVASIVE MEDICAL TREATMENT INSTALLATION

(75) Inventors: Rainer Kaltschmidt, Eckental/Brand (DE); Ulrich Will, Kunreuth (DE)

(73) Assignee: Siemens Aktiengesellschaft, Munich (DE)

( * ) Notice: Subject to any disclaimer, the term of this patent is extended or adjusted under 35 U.S.C. 154(b) by 24 days.

(21) Appl. No.: 10/588,669

(22) PCT Filed: Feb. 14, 2005

(86) PCT No.: PCT/EP2005/050629

§ 371 (c)(1),
(2), (4) Date: Aug. 7, 2006

(87) PCT Pub. No.: WO2005/082260

PCT Pub. Date: Sep. 9, 2005

(65) Prior Publication Data

US 2007/0183570 A1    Aug. 9, 2007

(30) Foreign Application Priority Data

Mar. 1, 2004    (DE) .................. 10 2004 010 004

(51) Int. Cl.
*A61B 5/05* (2006.01)
(52) U.S. Cl. ...................................... 600/427
(58) Field of Classification Search ................ 600/427; 601/2, 4; 378/65
See application file for complete search history.

(56) References Cited

U.S. PATENT DOCUMENTS

| 4,971,039 A | 11/1990 | Noske et al. |
|---|---|---|
| 5,044,354 A | 9/1991 | Goldhorn et al. |
| 5,199,420 A | 4/1993 | Artmeier |
| 6,461,039 B1 * | 10/2002 | Klotz et al. .................. 378/197 |
| 2003/0078523 A1 | 4/2003 | Burkhardt et al. |

FOREIGN PATENT DOCUMENTS

| DE | 198 08 402 | 9/1999 |
|---|---|---|
| DE | 101 06 832 | 8/2002 |
| DE | 103 03 462 | 8/2004 |
| DE | 10 2004 010 005 | 9/2005 |

* cited by examiner

*Primary Examiner*—Eric F Winakur
*Assistant Examiner*—Michael T Rozanski
(74) *Attorney, Agent, or Firm*—Schiff Hardin LLP

(57) ABSTRACT

A non-invasive medical treatment installation has a therapy C-arm mounted on a base, and defining an isocenter. A therapy apparatus having a focus is mounted at the free end of a carrier arm, that has a fixed end attached to the therapy C-arm. The mounting of the fixed end of the carrier arm to the therapy C-arm allows orbital movement of the carrier arm along the therapy C-arm between two final positions respectively delimited by the opposite ends of the C-arm. The carrier arm is mounted to the therapy C-arm to allow rotation of the carrier arm around a rotational axis, so that when the carrier arm is at either of said final positions, it extends beyond the respective end of the C-arm.

5 Claims, 6 Drawing Sheets

NON-INVASIVE MEDICAL TREATMENT INSTALLATION

BACKGROUND OF THE INVENTION

1. Field of the Invention

The present invention concerns a system for non-invasive medical treatment of the type wherein a therapy apparatus (such as a shockwave head in the case of a lithotripsy treatment) is moved on an orbit around a patient table or around a patient on this patient table.

2. Description of the Prior Art

A body region of the patient to be treated in a system of the above type is arranged in the isocenter of the orbit. The focus of the therapy apparatus (in the case of a shockwave head thus the focus of the ultrasonic waves emanating therefrom) is located in the isocenter or in the body region to be treated. A circular arc, known as a C-arm, is generally used for guidance of the therapy apparatus. In the case of a C-arm that is permanently fixed at a base, this C-arm must exhibit an arc length that is at least as large as the desired movement path of the therapy apparatus. The arc length of the C-arm can be shortened if it is supported so that it can be moved orbitally on the base. A therapy apparatus movably guided on a C-arm has the advantage that it can be positioned on different sides of the body of a patient without the patient having to be repositioned on the patient table. A system of this type is normally designed such that the base and further system parts are arranged on one side of the patient table, so the other side of the patient table can remain essentially free in order to allow unhindered access to the patient (such as for anesthesia purposes). If a therapy apparatus should now be brought into position on this side of the patient table, the therapy apparatus itself is less disruptive than the C-arm because the therapy apparatus is positioned relatively close to the patient. If, for example, a shockwave head is positioned in the 0° position (i.e. in the upper table position given vertical alignment of its shockwave axis) for lithotripsy treatment, the C-arm extends into the space above the patient at least up to this angle position. A treating doctor is thereby severely limited in terms of his or her freedom of movement in the region of the doctor's head.

SUMMARY OF THE INVENTION

An object of the present invention is to provide a system for non-invasive medical treatment wherein the aforementioned disadvantage is avoided.

This object is achieved according to the invention by a therapy system having a carrier arm with a fixed end and a free end mounted on the therapy C-arm, the fixed end of the carrier arm being supported on the therapy C-arm between two end positions predetermined by the arc ends such that the carrier arm with its fixed end can move in an orbit. The carrier arm supports the therapy apparatus on its free end. The carrier arm is furthermore supported on the therapy C-arm such that it can rotate around a rotation axis, so it can be aligned at both end positions such that it extends beyond the respective arc end. The rotatable support of the carrier arm on the therapy C-arm ensures that such a projection beyond the arc end can also be produced in a simple manner at the other end position.

The rotation axis of the carrier arm is preferably aligned such that it intersects the focus of the therapy apparatus. It is thereby ensured that, given a rotation of approximately 180° around the rotation axis of the therapy focus, its position is not altered. This position typically lies in the isocenter of a C-arm. The position of the therapy focus is thus altered neither by an orbital movement of the carrier arm nor by a rotation around the rotation axis.

In a further preferred embodiment, the therapy apparatus is arranged such that its focus is located in a plane that runs parallel to and removed from the orbital plane of the therapy C-arm. This makes it possible to remove the effective location of the therapy apparatus from the orbital plane of the therapy C-arm and thereby to achieve even more freedom of movement in the region of the therapy C-arm for a person attending the patient. This embodiment is particularly advantageous when, for imaging accompanying a treatment, an x-ray C-arm is arranged coaxial, coplanar and with axial offset relative to the therapy C-arm, the focus of the therapy apparatus coinciding with the isocenter of the x-ray C-arm. In addition to the increased freedom of movement (already mentioned) for medical personnel, this achieves the advantage that the x-ray C-arm can in practice be moved orbitally without hindrance. In an arrangement of x-ray and therapy C-arms in which the orbital planes of both arcs coincide, the orbital movement capability of the x-ray C-arm is significantly limited, for example because x-ray source or x-ray receiver protrude into the movement path of the therapy C-arm.

DESCRIPTION OF THE PREFERRED EMBODIMENTS

Figure 1:
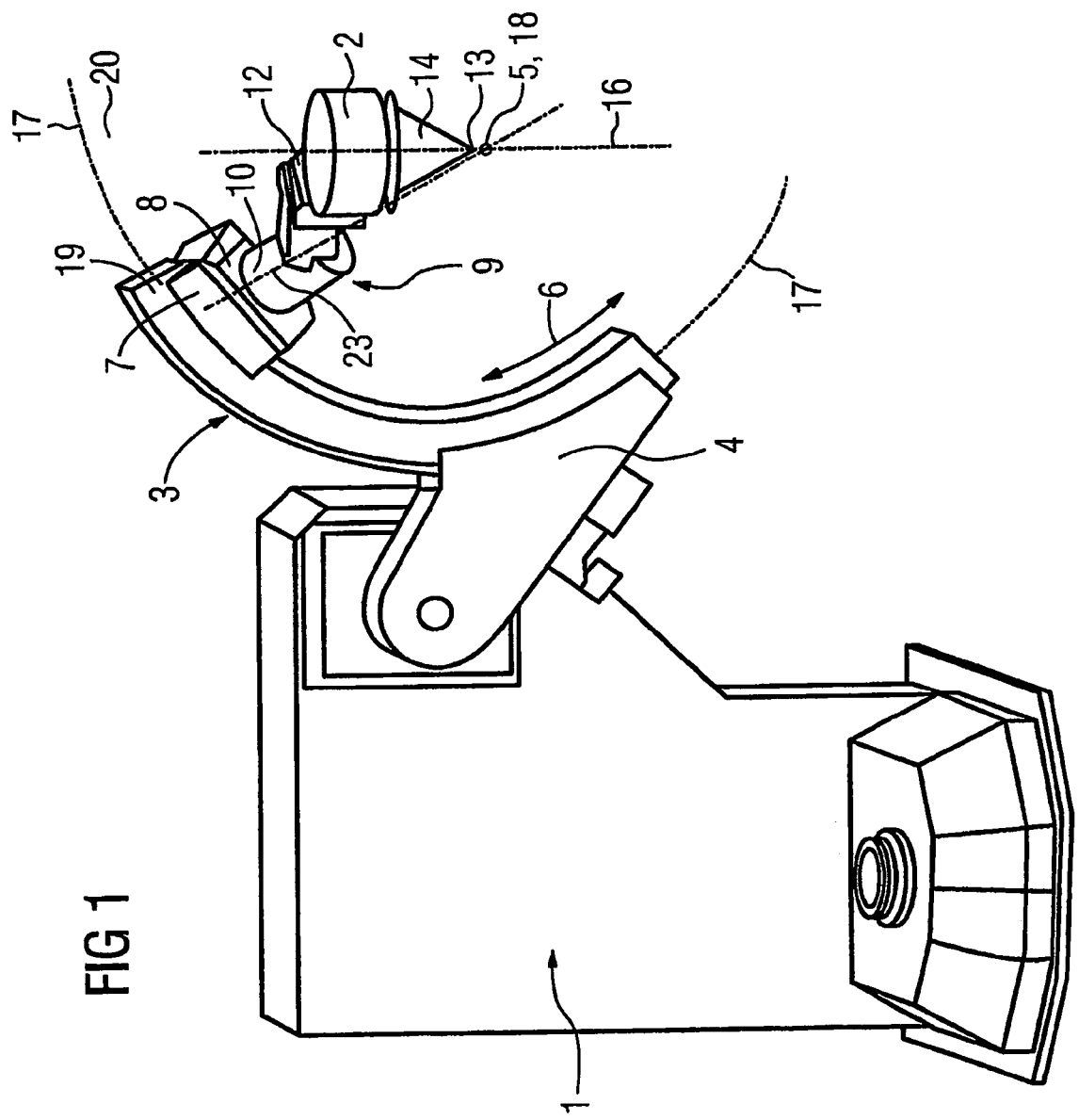
FIG. 1 is a perspective view of a base for a therapeutic treatment system in accordance with the invention, on which a therapy C-arm is supported that carries a therapy apparatus, the C-arm being supported so as to be able to move orbitally around an isocenter.

The system shown in the Figures has a base 1 on which is fixed a first C-arm that supports a therapy apparatus (for example the shockwave head 2 of a lithotripsy system). The first C-arm (designated in the following as therapy C-arm 3) is an annulus segment that can be orbitally moved on an extension arm 4 of the base frame 1 around its middle point or around its isocenter 5, which is indicated in FIG. 1 by the double arrow 6. A sled 7 is supported on the therapy C-arm 3 such that it can move orbitally (thus corresponding to double arrow 6). A carrier arm 9 is attached with its fixed end 10 on a side 8 of the sled 7 facing the isocenter 5. The free end 12 of the carrier arm 9 carries the shockwave head 2. Due to the orbital movement capability of the therapy C-arm 3 and the sled 7, the shockwave head 2 can be positioned in various angle positions relative to the isocenter 5 or to a patient table 15. The radial separation of the shockwave head 2 from the isocenter 5 is selected such that the focus 13 of a shockwave cone 14 emitted from the shockwave head 2 lies on a central axis 18 extending through the isocenter 5. The shockwave head 2 can, for example, be arranged such that the shockwave axis 16 thereof proceeds in the orbital plane 17 spanned by the therapy C-arm 3.

Figure 2:
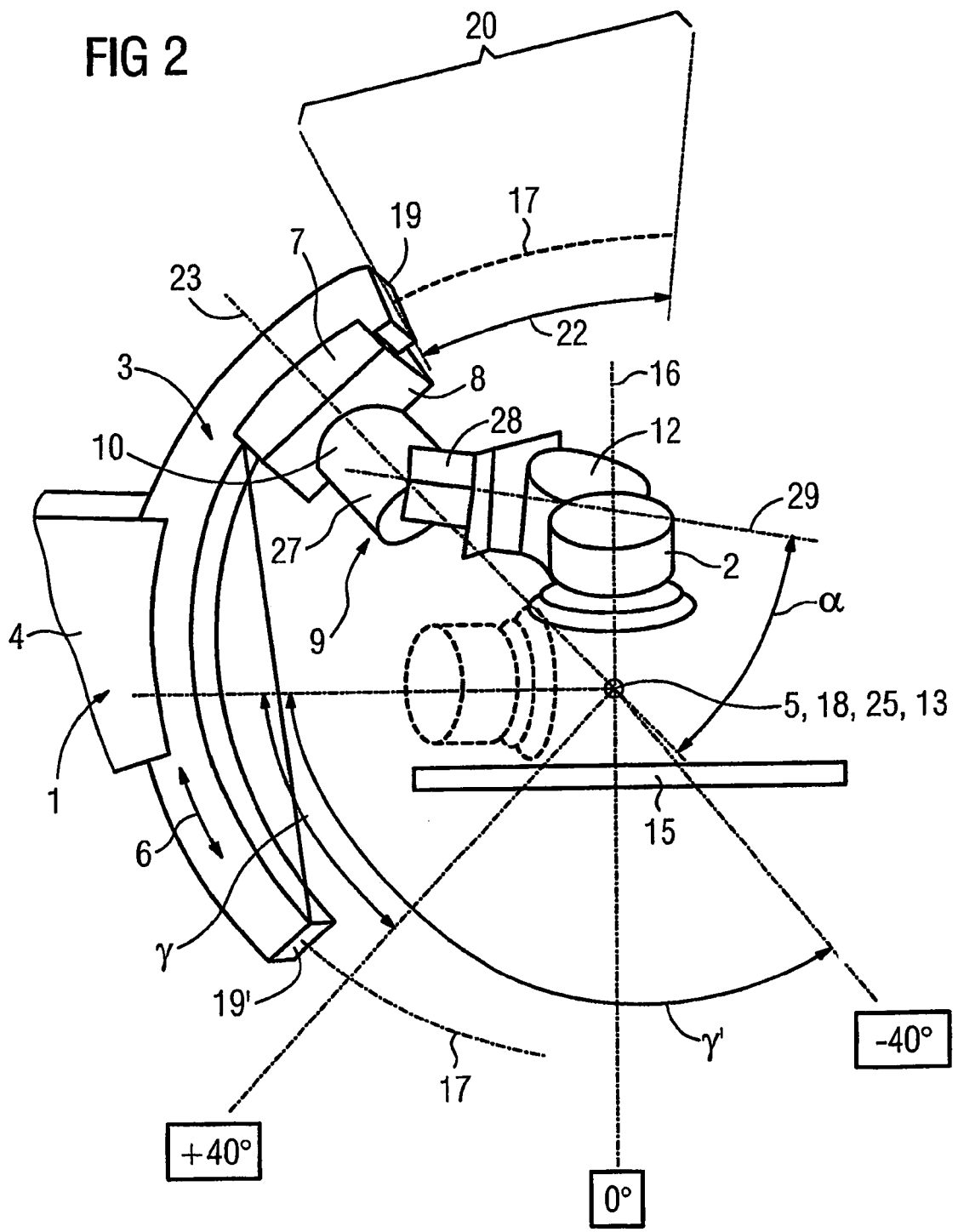
FIG. 2 is a perspective view of a portion of the system of FIG. 1.

As can be seen from FIG. 1 and in particular from FIG. 2, the carrier arm 9 is designed or aligned such that, in its upper end position (FIG. 2), it extends beyond the upper arc end 19 in the arc circumference direction, viewed in the direction of the central axis 18 situated perpendicular to the orbital plane 17 and extending through the isocenter 5. An unhindered accessible space 20 in the head region of a person attending a patient during the treatment thus exists above the shockwave head 2. If the carrier arm (likewise seen in the projection of FIG. 2) were aligned approximately in the direction of the shockwave axis 16, thus radially, the therapy C-arm 3 would have to be longer by approximately the arc segment 22 or would have to be orbitally moved further by a corresponding length, whereby it would limit the freedom of movement of an attending person in the space 20.

Figure 3:
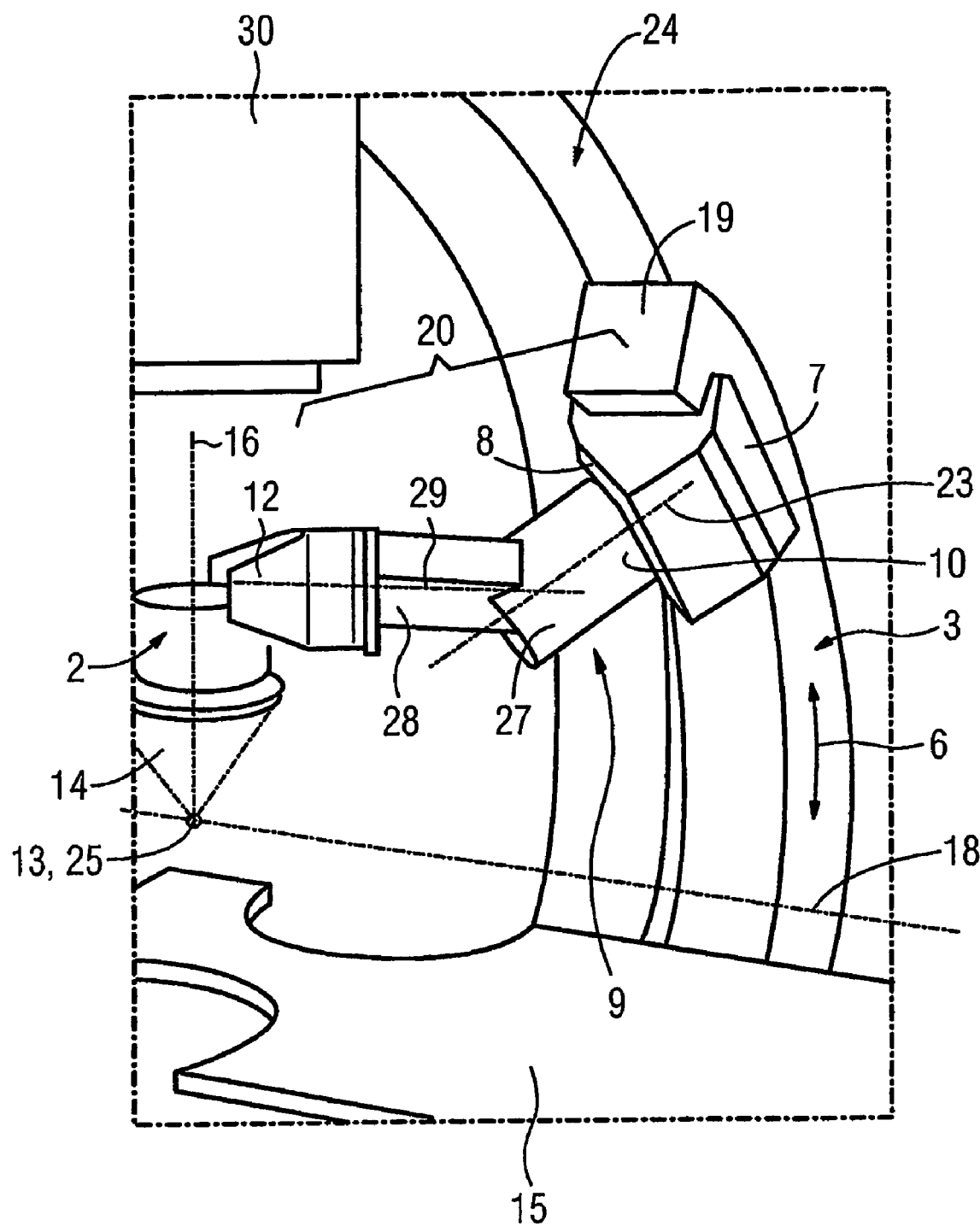
FIG. 3 is a further perspective view of a further embodiment of a system in accordance with the present invention, wherein an x-ray C-arm is associated with the therapy C-arm.
Figure 6:
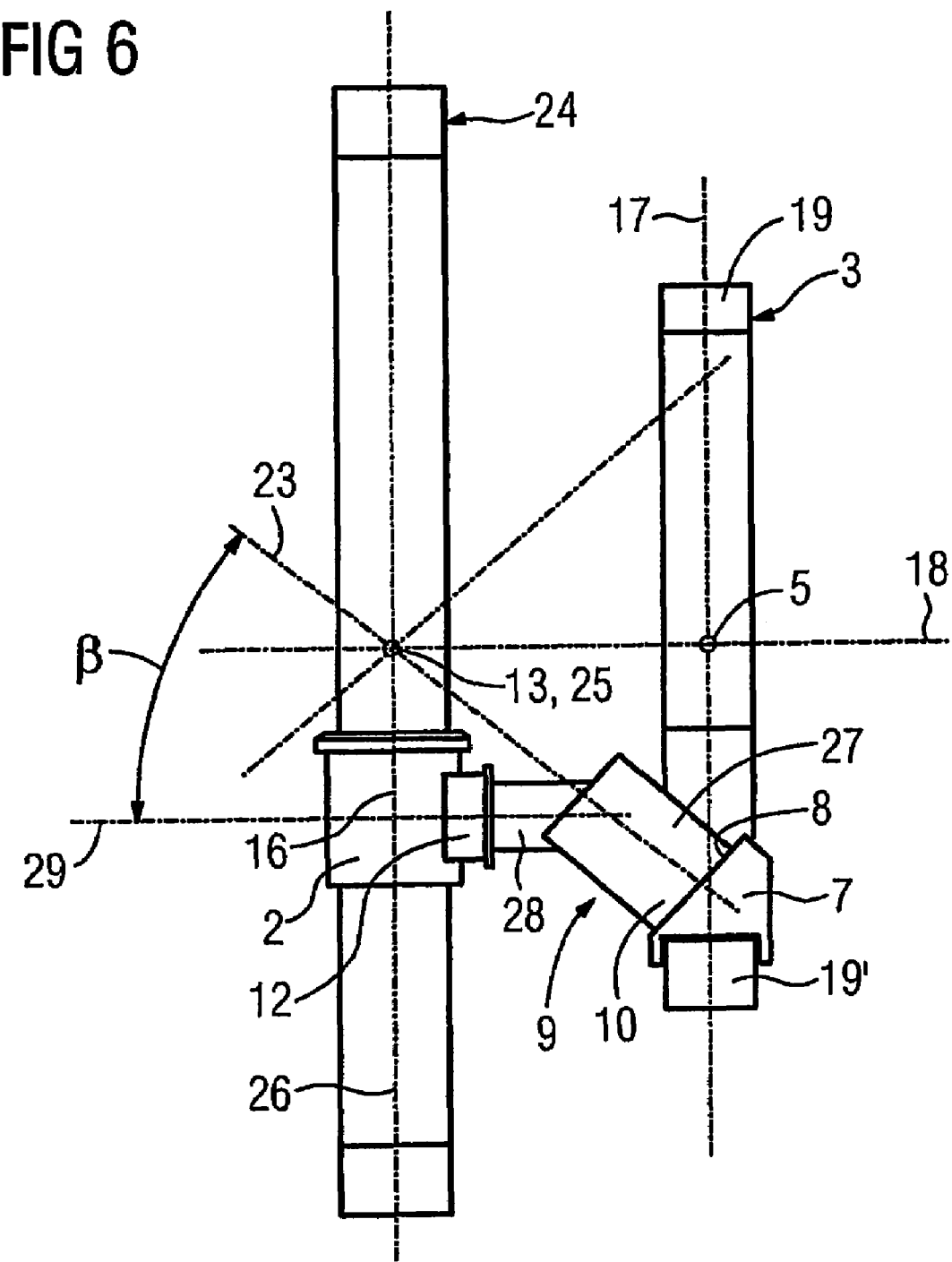
FIG. 6 schematically illustrates the therapy C-arm and the x-ray C-arm of the embodiment of FIG. 4.

So that both the therapy C-arm 3 and the sled 7 of the carrier arm 9 also overhang the lower arc end 19' in the arc circumference direction in the lower end position, the carrier arm 9 is supported on the sled 7 such that it can rotate around a rotation axis 23. It would now be possible for not only a single rotation axis to be present, but also for the shockwave head 2 also to exhibit a degree of freedom relative to the carrier arm 9. The purpose of such a movement capability would be to bring the shockwave head 2 back into a position in which its focus 13 again comes to lie on the central axis 18 (for example coincides with the isocenter 5 of the therapy C-arm 3) after cycling an orbital movement path. Such multiple movement possibilities or articulation points, however, form error sources with regard to an exact alignment of the shockwave head 2 as a result of tolerances that can never be entirely precluded given parts that are movably connected with one another. In the described exemplary embodiments, the shockwave head 2 is therefore rigidly connected with the carrier arm 9, which is likewise rigidly fashioned. The rotation of the carrier arm 9 ensues around a single axis, namely the rotation axis 23. Given a rotation of 180° around this axis, the carrier arm (like the shockwave head) is located in a mirror-inverted alignment relative to the previous position, with the rotation axis 23 forming the mirror axis. For x-ray-supported observation of, for instance, a lithotripsy treatment, the therapy C-arm can be provided with an x-ray C-arm coaxial therewith, having an x-ray source (not shown) and an x-ray receiver 30 without or with axial offset. In the first case, the orbital planes and the isocenters of both C-arms coincide. The rotation axis 23 of the C-arm 9 proceeds in the common orbital plane of the C-arms and extends through their common isocenter. The shockwave head 2 thus can be aligned such that its shockwave axis 16 proceeds in the common orbital plane. Given a rotation around the rotation axis 23 by 180°, upon transition from one end position into the other the shockwave head 2 again adopts a position in which its shockwave axis 16 runs in the orbital plane 17 of the therapy C-arm 3. The monitoring with the x-ray system can then ensue "inline" in each angle position, i.e. in the direction of the shockwave axis 16. In the second case shown in the figures, the x-ray C-arm 24 is arranged with axial separation from the therapy C-arm 3. Its isocenter 25, like the isocenter 5 of the therapy C-arm 3, lies on the central axis 18. As can be seen from FIG. 3 and FIG. 6, the carrier arm 9 extends laterally out of the orbital plane 17. The shockwave head 2 fixed at the free end 12 of the carrier arm 9 is then arranged in the region of the orbital plane 26 of the x-ray C-arm 24, with its focus 13 located in its isocenter 25. The shockwave head 2 can be aligned such that its shockwave axis 16 proceeds in the orbital plane 26 of the x-ray C-arm 24 in one angle position per side. However, this alignment changes given a rotation around the rotation axis 23, meaning that the shockwave axis 16 is tilted out of the orbital plane 26, but, in accordance with the invention, the common isocenter is retained.

Figure 4:
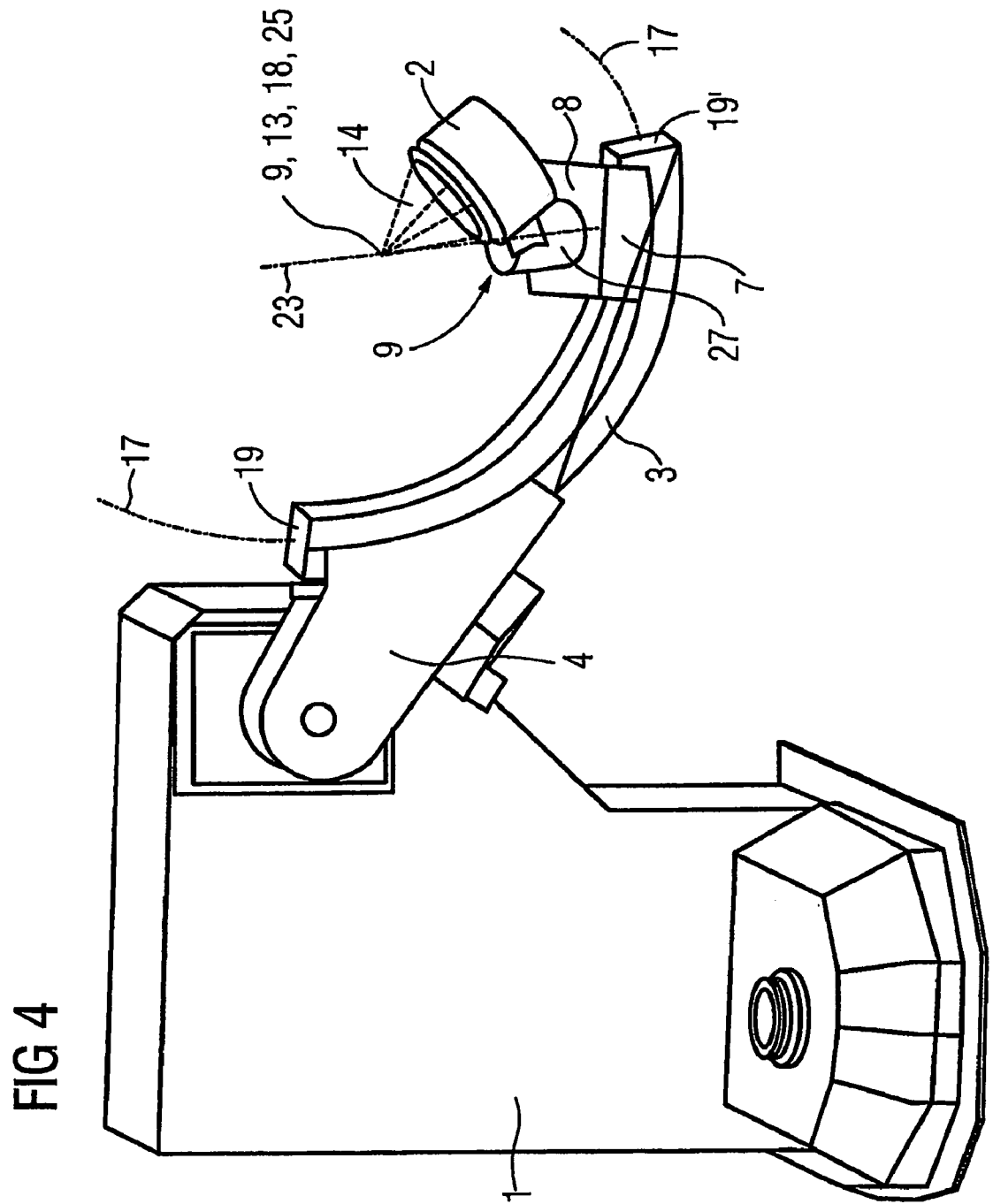
FIG. 4 shows the system of FIG. 1, with the therapy apparatus located in a different position.
Figure 5:
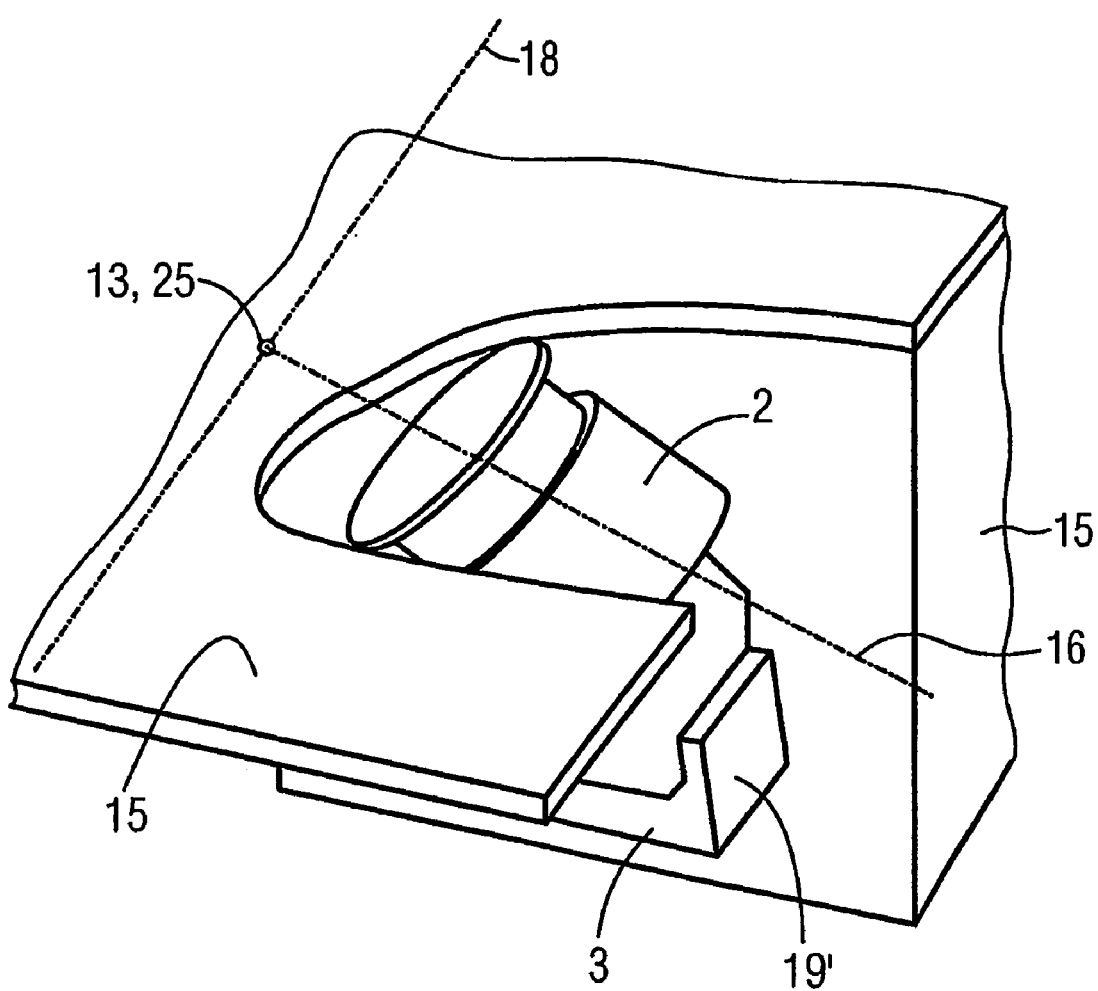
FIG. 5 shows a portion of the system of FIG. 4 with the therapy apparatus in a treatment position.

The carrier arm 9 has a first longitudinal segment 27 with a fixed end 10 and a second longitudinal segment 28 with a free end 12. The longitudinal segment 27 is born on the sled 7 such that it can rotate. The rotation axis 23 (that is identical with the center longitudinal axis 29 of the longitudinal segment 27) pierces the orbital plane 17 of the therapy C-arm 3 with its one end and intersects the isocenter 25 of the x-ray C-arm 24. Given an orbital shift of the sled 7 on the therapy C-arm 3, the rotation axis 23 sweeps over the plane of a conical segment whose base surface is formed by the orbital plane 17 of the therapy C-arm and whose tip is formed by the isocenter 25 of the x-ray C-arm 24. The side 8 of the sled 7 from which the longitudinal section 26 projects proceeds at a right angle to the rotation axis 23. The second longitudinal segment 28 is fixed at an angle on the first longitudinal segment 27. Its center longitudinal axis 29 thereby forms an acute angle α (FIG. 2) with the rotation axis 23 in the projection on the orbital plane 17 and an acute angle β (FIG. 6) in the projection on a plane spanning from the examination axis 23 and the central axis 18. When, starting from the upper table position of the FIGS. 1-3, the shockwave head 2 should be moved into an under-table position (FIGS. 4-6), perhaps for treatment of a left or right kidney, two symmetrical operations are necessary, namely rotation by up to 180° around the rotation axis 23 and an orbital shift of the sled 7. Although both movement procedures can proceed simultaneously, they are described in succession for better comprehensibility. Starting from the situation in FIG. 2, if one initially begins with a rotation of 180° around the rotation axis 23 the shockwave head 2 subsequently, approximately adopts the position shown with dashed lines. As can be seen from FIG. 2, this corresponds to a rotation around the central axis 18. The focus 13 persists in the isocenter 25 given the rotation. The shockwave axis 16 thereby sweeps through a conical segment whose tip is the isocenter 25. Starting from the position shown in the dashed lines, an orbital shift by approximately 50° (angle γ) is necessary if the shockwave head 2 should, for instance, be aligned in the +40° position, and an orbital shift by, for instance, 130° (angle γ') is necessary for an alignment in the −40° position. In contrast to this, an orbital movement path of the sled 7 (likewise starting from the upper table position) of approximately 240° would be required given an approximately radially-aligned carrier arm extending in the direction of the shockwave axis 16. A therapy C-arm 3 with an arc length of more than 120° would be necessary for this. In contrast to this, given an inventive embodiment of the carrier arm 9 the therapy C-arm 3 can be shorted by, for instance, a piece corresponding to the arc segment 22.

Although modifications and changes may be suggested by those skilled in the art, it is the invention of the inventors to embody within the patent warranted heron all changes and modifications as reasonably and properly come within the scope of their contribution to the art.

We claim:

1. A system for non-invasive medical treatment comprising:
   a base;
   a therapy C-arm supported by said base for orbital movement relative to said base, and defining an isocenter;
   a therapy apparatus that emits therapeutic energy directed to a focus;
   a carrier arm having a fixed end slidably mounted to said therapy C-arm for orbital movement along said C-arm between two end positions respectively limited by opposite ends of said therapy C-arm, and having a free end at which said therapy apparatus is attached; and said carrier arm being mounted to said therapy C-arm for rotation around a rotation axis relative to said therapy C-arm and independently of the orbital movement allowing said carrier arm, when positioned at either of said opposite end positions, to extend beyond the respective end of said therapy C-arm so as to also extend the therapy apparatus beyond the respective end.

2. A system as claimed in claim 1 wherein said rotation axis of said carrier arm intersects said focus of said therapy apparatus.

3. A system as claimed in claim 1 wherein said therapy C-arm defines an orbital plane of said therapy C-arm, and wherein said therapy apparatus is mounted on said carrier arm to place said focus in a plane that is parallel to and spaced from said orbital plane.

4. A system as claimed in claim 3 comprising an x-ray C-arm, carrying x-ray imaging components, mounted to said base coaxially, coplanar with, and axially offset from, said therapy C-arm, said x-ray C-arm having an imaging isocenter and said therapy apparatus and said x-ray C-arm being oriented relative to each other so that said focus of said therapy apparatus coincides with said imaging isocenter.

5. A system as claimed in claim 1 wherein said therapy apparatus comprises a lithotripsy head that emits shockwaves converging at said focus.

* * * * *